United States Patent
O'Brien (10) Patent No.: US 7,079,903 B2
(45) Date of Patent: Jul. 18, 2006

(54) LOW POLARIZATION COATINGS FOR IMPLANTABLE ELECTRODES

(75) Inventor: Robert C. O'Brien, Sykesville, MD (US)

(73) Assignee: Greatbatch-Hittman, Inc., Columbia, MD (US)

( * ) Notice: Subject to any disclaimer, the term of this patent is extended or adjusted under 35 U.S.C. 154(b) by 77 days.

(21) Appl. No.: 10/792,315

(22) Filed: Mar. 3, 2004

(65) Prior Publication Data

US 2004/0176828 A1     Sep. 9, 2004

Related U.S. Application Data

(60) Provisional application No. 60/475,535, filed on Jun. 4, 2003, provisional application No. 60/451,423, filed on Mar. 3, 2003.

(51) Int. Cl.
    *A61N 1/05*    (2006.01)
(52) U.S. Cl. .................. 607/122; 607/116; 607/119; 600/374
(58) Field of Classification Search ........ 607/116–138; 204/192.15; 600/312–385
    See application file for complete search history.

(56) References Cited

U.S. PATENT DOCUMENTS

| | | | |
|---|---|---|---|
| 4,033,357 A | 7/1977 | Helland et al. | |
| 4,281,668 A | 8/1981 | Richter et al. | |
| 4,440,178 A * | 4/1984 | Bussard et al. | 607/121 |
| 4,495,039 A | 1/1985 | Cerise et al. | |
| 4,542,752 A * | 9/1985 | DeHaan et al. | 607/119 |
| 4,602,637 A | 7/1986 | Elmquist et al. | |
| 4,607,193 A | 8/1986 | Curren et al. | |
| 4,609,508 A | 9/1986 | Edeling et al. | |
| 4,612,100 A | 9/1986 | Edeling et al. | |
| 4,677,989 A * | 7/1987 | Robblee | 607/116 |
| 4,934,381 A | 6/1990 | MacGregor | |
| 5,074,313 A | 12/1991 | Dahl et al. | |
| 5,118,400 A | 6/1992 | Wollam | |
| 5,122,249 A | 6/1992 | Niemann et al. | |
| 5,147,590 A | 9/1992 | Preidel et al. | |
| 5,326,448 A | 7/1994 | Otten | |
| 5,482,602 A | 1/1996 | Cooper et al. | |
| 5,683,443 A * | 11/1997 | Munshi et al. | 607/121 |
| 5,980,973 A | 11/1999 | Onyekaba et al. | |
| 6,253,110 B1 | 6/2001 | Brabec et al. | |

(Continued)

FOREIGN PATENT DOCUMENTS

EP     0 453 117 A1     10/1991

OTHER PUBLICATIONS

M Mohanty, TV Anilkumar, PV Mohanan, CV Muraleedharan, GS Bhuvaneshwar, F Derangere, Y Sampeur. Long term tissue response to titanium coated with diamond like carbon. Biomol Eng 2002; 19(2-6): 125-128. □□*

(Continued)

*Primary Examiner*—Robert E. Pezzuto
*Assistant Examiner*—Tammie Heller
(74) *Attorney, Agent, or Firm*—Michael F. Scalise (57) ABSTRACT

Coatings for implantable electrodes such as pacing electrodes, neurostimulator electrodes, and electroporating electrodes and sensing electrodes are described. The coatings are highly biocompatible, having low polarization. They consist of a biocompatible, conductive substrate, such as of sintered platinum/10% iridium; a thin film outer layer of biocompatible, conductive carbon; and a biocompatible, conductive intermediate layer having a high surface area. The intermediate layer is preferably of sputtered titanium nitride and increases the surface area of the carbonaceous outer layer.

17 Claims, 6 Drawing Sheets

U.S. PATENT DOCUMENTS

| | | | |
|---|---|---|---|
| 6,292,704 B1* | 9/2001 | Malonek et al. | 607/121 |
| 6,328,857 B1 | 12/2001 | Anzaki et al. | |
| 6,430,447 B1 | 8/2002 | Chitre et al. | |
| 6,464,889 B1 | 10/2002 | Lee et al. | |
| 6,799,076 B1* | 9/2004 | Gelb et al. | 607/121 |
| 6,901,297 B1* | 5/2005 | Frericks et al. | 607/121 |
| 2004/0127966 A1* | 7/2004 | Frericks et al. | 607/116 |
| 2005/0075708 A1* | 4/2005 | O'Brien et al. | 607/116 |

OTHER PUBLICATIONS

M Allen, B Myer, N Rushton. In vitro and in vivo investigations into the biocompatibility of diamond-like carbon (DLC) coatings for orthopedic applications. J Biomed Mater Res 2001; 58: 319-328.*

FZ Cui and DJ Li. A review of investigations on biocompatibility of diamond-like carbon and carbon nitride films. Surf Coat Technol 2000; 131: 481-487.*

Biomed. Technik 34 (1989), 185-190, M. Schaldach, M. Hubmann, R. Hardt, A. Weikl, Pacemaker Electrodes Made of Titanium Nitride.

Medical Progress Through Technology 21 (1995) Feb., No. 1, Dordrecht, NL M. Schaldach-New Aspects in Electrostimulation of the Heart.

* cited by examiner

LOW POLARIZATION COATINGS FOR IMPLANTABLE ELECTRODES

CROSS-REFERENCE TO RELATED APPLICATIONS

The present application claims priority from U.S. provisional application Ser. Nos. 60/451,423, filed Mar. 3, 2003 and 60/475,535, filed Jun. 4, 2003.

BACKGROUND OF THE INVENTION

1. Field of the Invention

This invention generally relates to coatings for implantable electrodes such as pacing electrodes, neurostimulator electrodes, and electroporating electrodes and sensing electrodes. The coatings are highly biocompatible, having low polarization. They consist of a biocompatible, conductive substrate; a thin film outer layer of biocompatible, conductive carbon; and a biocompatible, conductive intermediate layer having a high surface area. The intermediate layer increases the surface area of the carbonaceous outer layer.

2. Prior Art

Three overriding requirements for implantable electrodes are biocompatibility, biostability, and low energy loss. Broadly, the biocompatibility requirement is met if contact of the electrode with body tissue and blood results in little or no immune response from the body, especially thrombogenicity (clotting) and encapsulation of the electrode with fibrotic tissue. The biostability requirement means that all physical, electrical, and chemical properties of the electrode/coating system remain constant and unchanged over the life of the patient. The low energy loss requirement is met if electrode polarization is a minimum.

In the patent literature, U.S. Pat. No. 4,602,637 to Elmqvist describes a commonly used pacing electrode having sputtered columnar titanium nitride as a coating material. This form of titanium nitride has good conductivity combined with a high specific surface area, resulting in favorable polarization and sensing properties. The disadvantage of titanium nitride, however, is that it degrades the electrical properties of surrounding tissue after implantation. This occurs as the body tissue encapsulates the columnar titanium nitride in fibrotic tissue, which has a lower conductivity than normal tissue.

In the case of a pacing electrode, fibrotic tissue raises the stimulation threshold. The stimulation threshold is the minimum energy required to produce a cardiac contraction. A raised stimulation threshold, in turn, impacts the battery life of the system so that the medical device must be explanted sooner than desired. The encapsulation process also interferes with sensing of intrinsic millivolt signals required by pacemakers. In prior electrode designs, the fibrotic encapsulation problem has been addressed by incorporating a means of metering or eluting steroidal medication to the tissue contact site over time.

However, steroidal medication is not completely effective in eliminating the stimulation threshold rise due to encapsulation. Steroidal medication eluting arrangements have a relatively short duration of effectiveness, and also add cost and complexity to the system, add risk of infection, and, in many cases, a portion of the electrode working surface must be dedicated to the medication administering function.

The problem of encapsulation has also been addressed by the use of carbon as an electrode material. Carbon is much more highly biocompatible than the previously used noble metals and valve metals. For example, U.S. Pat. No. 4,033,357 to Helland et al. describes the use of pyrolitic carbon for pacing electrodes, although no means of increasing the surface area is discussed. In that regard, pacing electrode designs according to this patent meet the requirement of improved biocompatibility, but they do not have the high specific surface characteristics of currently used columnar titanium nitride.

Various methods of reducing the polarization of implantable carbon electrodes by increasing their surface area have also been tried. U.S. Pat. No. 4,281,668 to Richter et al. describes one method comprising heating glassy carbon parts in air to form a porous layer of increased surface area. Gluing the glassy carbon to the electrode stem completed the electrode assembly. Another method is described in U.S. Pat. No. 4,612,100 to Edeling et al. in which high sputter power levels are used to induce porosity on the order of 20 angstroms in sputtered carbon films. U.S. Pat. No. 4,609,508 to Edeling et al. also noted that microscopic porosity is induced in the course of the pyrolytic processing of vitreous carbon. Still more efforts to increase the surface area of carbon thin films in pacing electrodes are described in U.S. Pat. No. 5,074,313 to Dahl et al. This patent teaches sputtering a carbon thin film over a layer of high surface area sputtered metallic aluminum. A similar method is described in U.S. Pat. No. 5,118,400 to Wollam in which metallic titanium, aluminum, or zirconium as high surface area materials are sputtered to a "hillocked" morphology.

In addition to increasing the surface area, U.S. Pat. No. 4,495,039 to Cerise et al. shows that polaraization of pyrocarbon electrodes can be reduced by means of electrochemical activation of the carbon surfaces. This is done by immersing the carbonaceous material in concentrated acid and imposing an electrical current thereto.

Thus, there is still a need for an implantable electrode construction having the requisite improved biocompatibility along with high specific surface characteristics, such as provided by columnar titanium nitride. The present electrode fulfills this need in terms of both low polarization and minimum energy requirements for acceptable sensing properties.

SUMMARY OF THE INVENTION

Figure 1:
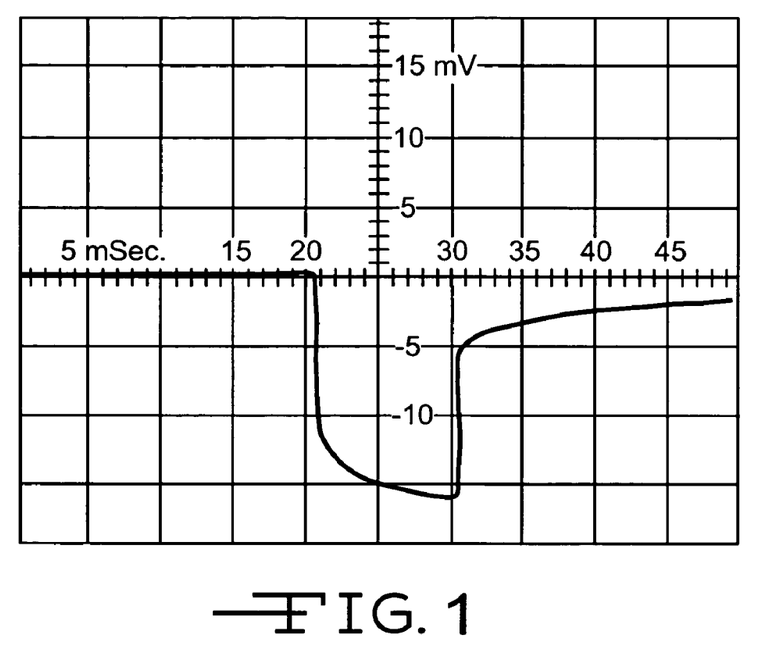
FIG. 1 is an oscilloscope graph of the voltage response of a pacing electrode only provided with a sintered platinum/ iridium alloy powder coating and no other.
Figure 2:
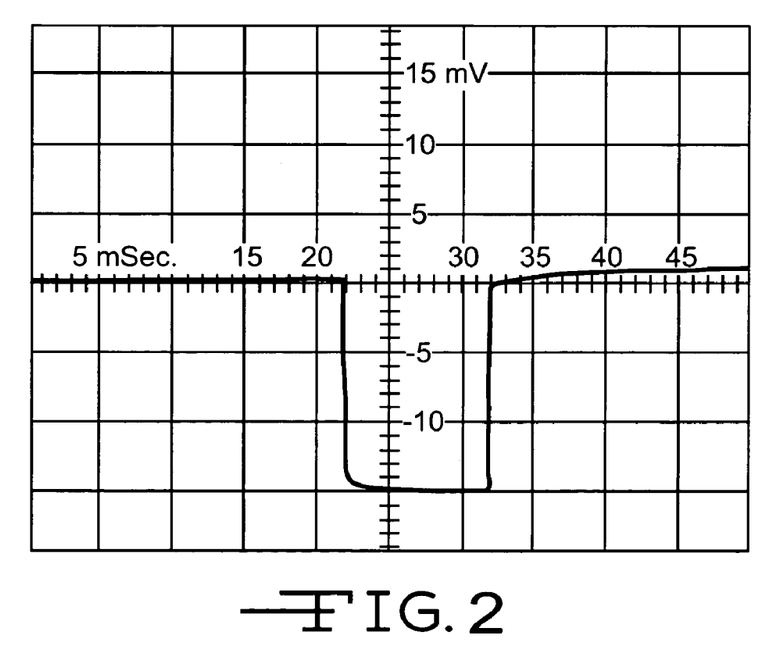
FIG. 2 is an oscilloscope graph of the voltage response of a pacing electrode provided with a sintered platinum/iridium alloy powder coating in turn provided with a titanium nitride intermediate layer and an outer layer of sputtered amorphous carbon.

Electrode polarization is defined as the residual voltage at the end of a voltage pulse across the electrode/tissue interface. FIGS. 1 and 2 show oscilloscope traces of the voltage response of pacing electrodes to a 10 msec square wave pulse in a saline electrolyte. In both cases, the electrode is coated with a sintered platinum/iridium alloy. In the former graph, the electrode-sintered layer is not further coated and the polarization is >−400 mV. The platinum/iridium alloy sintered coating in the latter graph is further provided with a coating of porous titanium nitride having an outer layer of sputtered amorphous carbon according to the present invention. The polarization reading is >−45 mV.

The present electrode exhibits relatively low polarization because of the greatly increased surface area imparted by the sputtered carbon, which mimics the physical structure of conventional sputter coated columnar titanium nitride. Furthermore, the present electrode is both biocompatible and biostable because the sputtered carbon coating is strongly adherent and chemically inert. In that light, the excellent biocompatibility of sputtered carbon lessens or eliminates the requirement for providing steroidal medication to the tissue surrounding the electrode.

These and other aspects of the present invention will become increasingly apparent to those skilled in the art by reference to the following description and to the appended drawings.

DETAILED DESCRIPTION OF THE PREFERRED EMBODIMENTS

Figure 3:
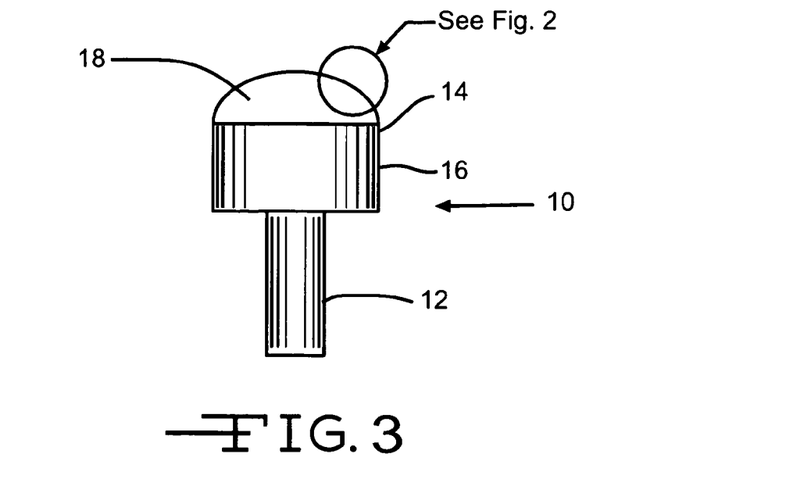
FIG. 3 is a side elevational view of a machined electrode 10.
Figure 4:
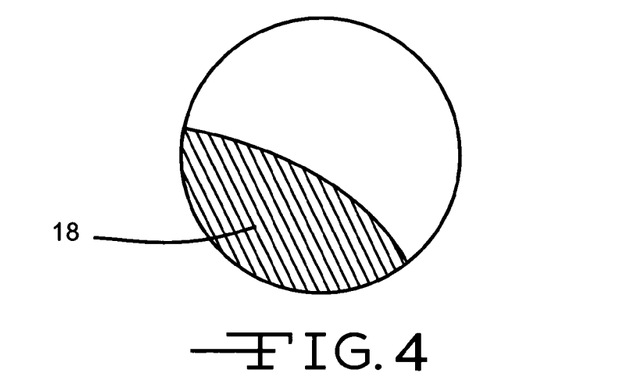
FIG. 4 is an enlarged view of the indicated area in FIG. 3.
Figure 5:
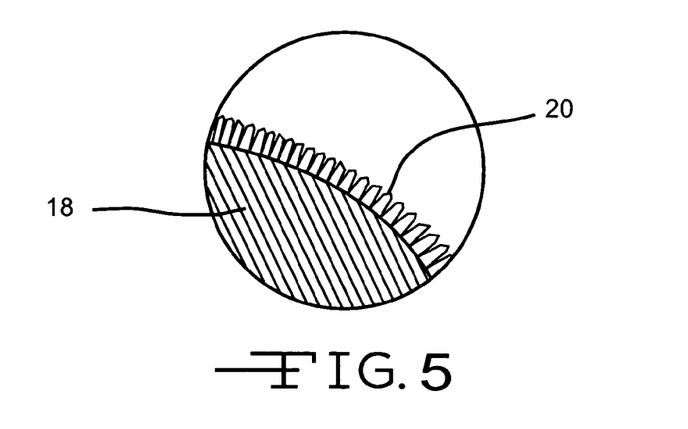
FIG. 5 is an enlarged, cross sectional view of the electrode in FIGS. 3 and 4 provided with an electrically conductive, biocompatible, high surface area layer 20.
Figure 6:
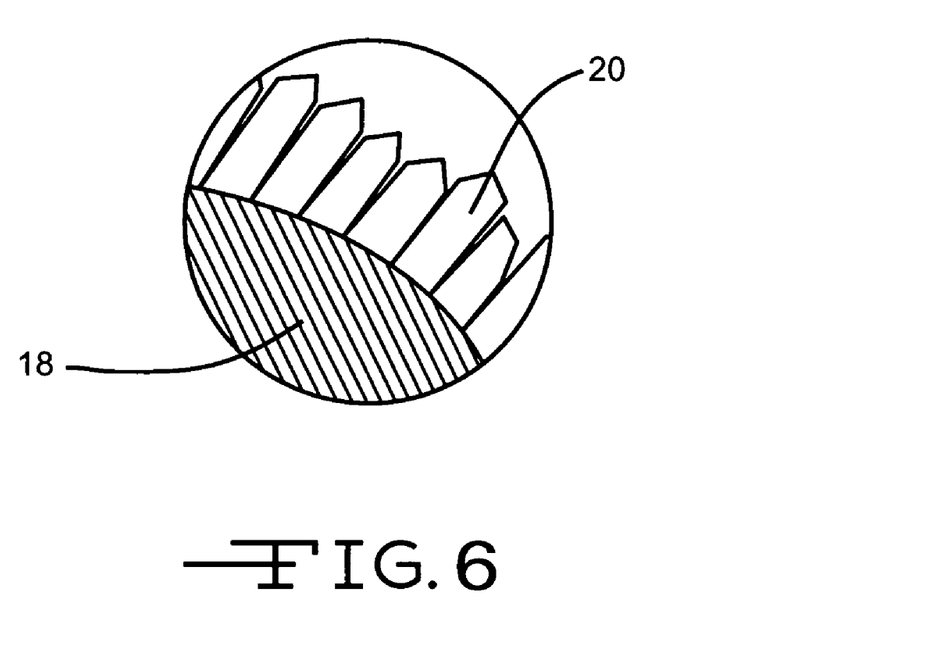
FIG. 6 is an enlarged view of FIG. 5.

Referring now to the drawings, FIGS. 3 and 4 illustrate a machined electrode 10 comprising a stem 12 supporting an integral tip or head 14. The electrode is of a material selected from tantalum, titanium, zirconium, iridium, platinum, and niobium. Preferably, the electrode is of platinum/10% iridium. The electrode head 14 has a cylindrically shaped portion 16 forming into a curved or dome-shaped active surface 18. As shown in FIGS. 5 and 6, a biocompatible, electrically conductive, high surface area layer 20 is formed over the active substrate surface 18. The thickness of layer 20 is about 0.1 micrometers (µm) to about 20 µm, preferably about 5 µm. The high surface area layer 20 increases the effective surface area of the electrode head 14.

Figure 7:
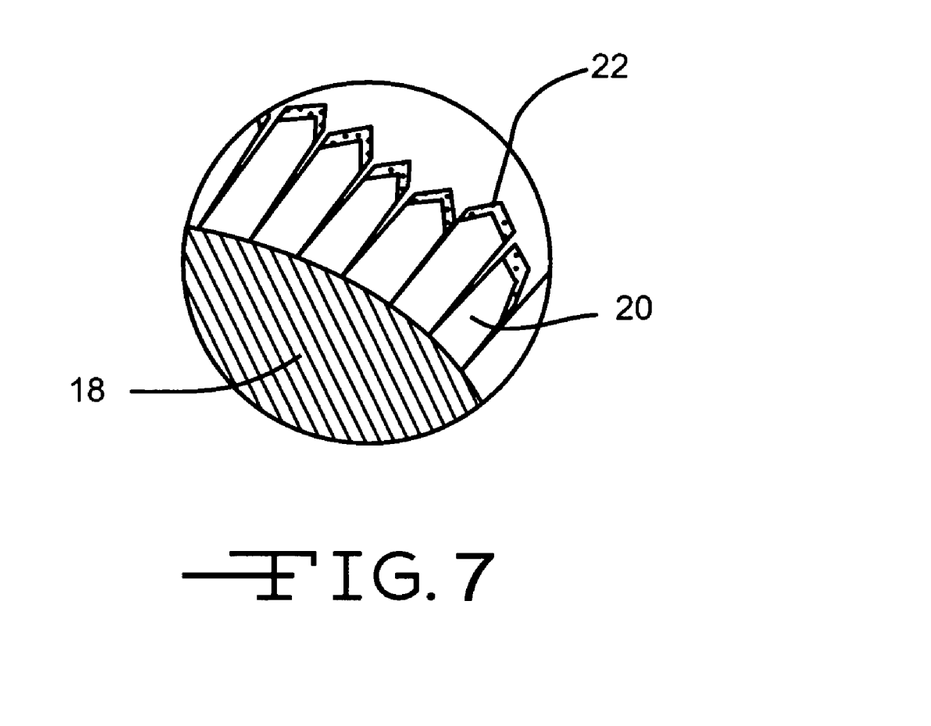
FIG. 7 is an enlarged view of the electrically conductive, biocompatible, high surface area layer of FIGS. 5 and 6 provided with an amorphous carbon outer layer 22.

FIG. 7 shows an outer layer 22 consisting of amorphous carbon having been coated over the high surface area intermediate layer 20. The amorphous carbon outer layer 22 is preferably applied by physical vapor deposition to a thickness of about 10 nanometers (nm) to about 1.0 µm, and preferably about 0.2 µm thick. Depositing by a physical vapor means takes advantage of the intrinsic low polarization and high biocompatibility of amorphous carbon while exploiting the ability of a thin film of this material to conform to the roughness of the high surface area active layer 20. Conforming to the underlying intermediate layer 20 increases the surface area of the amorphous carbon outer layer 22. This means that rather than forming a continuous, pore free film over a substrate, the present invention takes advantage of the fact that physical vapor deposited thin films can be made to preserve any very fine scale porosity present in the substrate, including porosity having dimensions considerably less than the film thickness.

The intermediate active layer 20 can be any material that has high biocompatibility, biostability, and electrical conductivity. Examples include carbon, boron, platinum, iridium, gold, titanium, tantalum, niobium, ruthenium, zirconium, and alloys thereof. In addition, electrically or ionically conductive compounds of these metals; and alloys may be used, including iridium oxide, iridium nitride, titanium nitride, titanium carbide, titanium carbonitride, tantalum nitride, tantalum carbide, tantalum carbonitride, niobium carbide, niobium nitride, niobium carbonitride, ruthenium oxide, ruthenium nitride, zirconium oxide, zirconium nitride, zirconium carbide, and mixtures thereof. In cases where the compounds of the intermediate active layer 20 are not electrically conductive, they can be made so by doping with small amounts of extraneous elements. For example, titanium dioxide, a dielectric in its pure state, is made conductive by doping with niobium.

All of these intermediate active layer 20 materials can be applied to the machined electrode surface in such a way that the resulting coatings have high surface areas with very fine scale roughness and porosity. When these high surface area coatings are then coated with the conformal thin film carbon outer layer 22, their biocompatibility, biostability, and polarization characteristics are improved. It is also within the scope of this invention that doping the amorphous carbon outer layer 22 with nitrogen provides a further improvement to the electrode polarization. Nitrogen doping is preferably at a concentration of about 1 ppm to about 57 atomic percent.

Techniques useful for this purpose include sinter processing, micromachining, grit blasting, chemical etching, and the like. For example, some forms of carbon can be used to provide high surface area intermediate layers. These include sintered diamond doped with boron or, carbon nanotubes or fullerenes. Carbon nanotubes or fullerenes increase the conductivity of the machined electrode active surface 18 and can be grown in situ or attached to the electrode surface. Further disclosure regarding carbon nanotubes and fullerenes can be found in U.S. application Ser. No. 10/719, 632, filed Nov. 21, 2003, which is assigned to the assignee of the present invention and incorporated herein by reference.

Additionally, the machined electrode active surface 18 to which the intermediate high surface area active layer 20 is applied may itself have had its surface area increased.

As previously discussed, the preferred method of applying the thin film amorphous carbon outer layer 22 to the intermediate high surface area active layer 20 is by physical vapor deposition processes such as sputtering (deposition by plasma activation) or evaporation (deposition by thermally activated vaporization). However, the carbon overlayer 22 may also be applied in the form of pyrolytic carbon (thin film carbon thermally deposited by decomposing a liquid carbonaceous precursor), or by chemical vapor deposition (thin film carbon thermally deposited by decomposing a gaseous carbonaceous precursor) methods. The resulting carbon outerlayer may then range in atomic structure from glassy (a completely amorphous, random structure with no covalent bonding) to turbostratic (microcrystalline, short range order) to graphitic (crystalline with covalent bonding in two dimensions) to diamond (crystalline with covalent bonding in three dimensions).

As previously discussed, the thickness of the amorphous carbon outer layer 22 may vary from a few atomic layers to a micrometer, and more. The nature of the sputter deposition mechanism in particular allows the carbon overlayer film thickness to exceed the pore size of the high surface area active layer 20 by a factor of three or more while still preserving the high porosity, high surface area characteristic of this substrate. Moreover, a manufacturability advantage results from the ability to sequentially sputter the intermediate layer 20 and the outer amorphous carbon layer 22 with no additional handling of the electrodes between sputter process steps.

The effect is to provide an electrode coating 20, 22, which is biocompatible, and biostable, and which has advantageously low polarization because of the greatly increased surface area imparted to the carbon overlayer 22 by the intermediate high specific surface active layer 20. The excellent biocompatibility of the amorphous carbon coating has the advantage of providing a consistently low and stable stimulation threshold, which helps lessen or eliminate the requirement for providing steroidal medication to the tissue surrounding the implanted electrode 10.

The following examples describe the manner and process of a coated electrode according to the present invention, and set forth the best mode contemplated by the inventors of carrying out the invention.

EXAMPLE I

Platinum/20% Iridium Machined Electrode Provided with a Sintered Platinum/10% Iridium Coating Having a Titanium Nitride Intermediate Layer and a Sputtered Carbon Overlayer A number of machined electrodes comprising platinum/20% iridium provided with a sintered platinum/10% iridium coating were sputter coated with columnar titanium nitride (TiN) according to the previously discussed U.S. Pat. No. 4,602,637 to Elmquist et al. The sputter deposited titanium nitride had a high specific surface area due to its columnar structure with crystallite diameters of about 100 to about 500 nanometers A carbon overlayer was then applied to the titanium nitride coating by sputtering in argon using a carbon target. This consisted of placing the thusly processed electrodes in a Denton Vacuum LLC "Discovery" 18-deposition chamber. The chamber was evacuated to about $8 \times 10^{-7}$ torr prior to a 3.5 millitorr process gas being introduced therein. The process gas consisted of pure argon or 93% argon, 7% nitrogen, both at 105 SCCM. The platinum/20% iridium machined electrodes provided with the sintered platinum/10% iridium coating and having a 8 μm thick titanium nitride intermediate layer were then supported on an unheated, rotating table about four to five inches from a three-inch diameter piece of carbon (graphite) as a target. The magnetron cathode was set at 250 W DC and sputtering continued for 30 minutes. The thickness of the resulting carbon thin film was about 200 nm to about 300 nm.

The thusly-manufactured electrodes were then subjected to polarization testing and the results are set forth below:

| | |
|---|---|
| Sintered Pt/10% Ir only: | −440 mV |
| Sintered Pt/10% Ir with sputtered carbon coating: | −139 mV |
| Sintered Pt/10% Ir with sputtered TiN and a sputtered carbon overlayer, argon process gas: | −75 mV |
| Sintered Pt/10% Ir with sputtered TiN and a sputtered carbon overlayer, argon/7% nitrogen process gas: | −45 mV |

Figure 8:
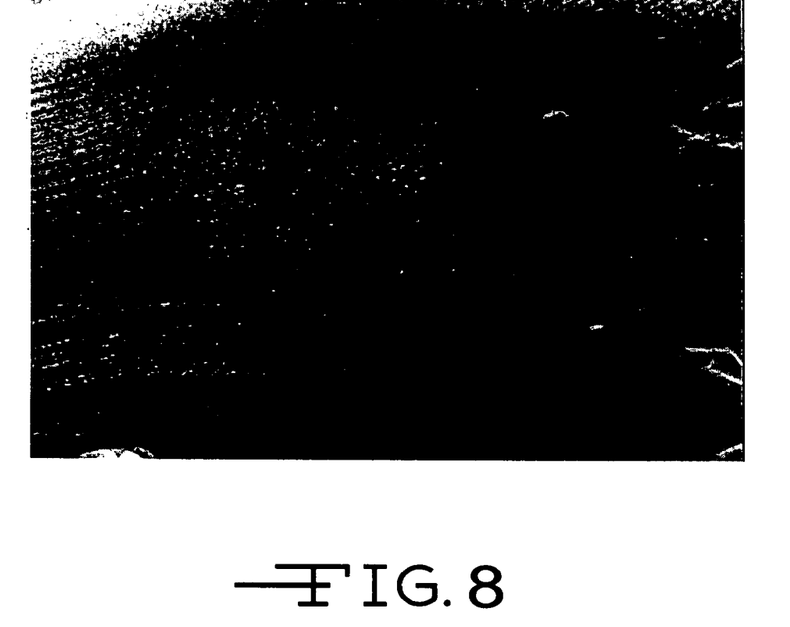
FIG. 8 is a photograph showing the surface of a single particle in a sintered platinum/10% iridium electrode coating with 200 nm thin film sputtered carbon coated directly on to the surface thereof. The width of field shown is 5.5 µm.
Figure 9:
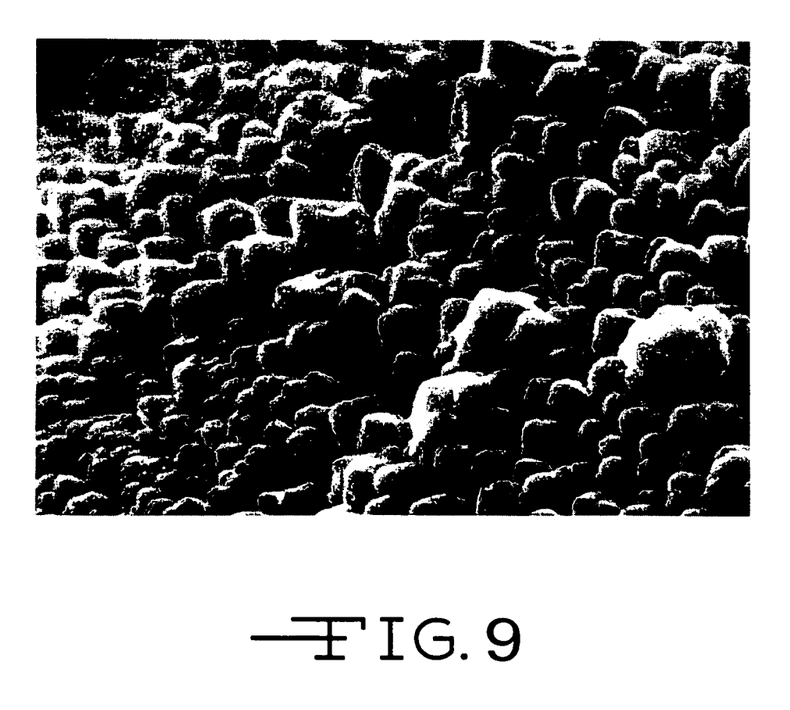
FIG. 9 is a photograph showing the surface of a platinum/ 10% iridium sintered particle, as shown schematically shown in FIG. 7, provided with a 200 nm thin film, nitrogen-doped carbon overlayer sputtered onto a titanium nitride intermediate layer. The width of field shown is 5.5 µm.
Figure 10:
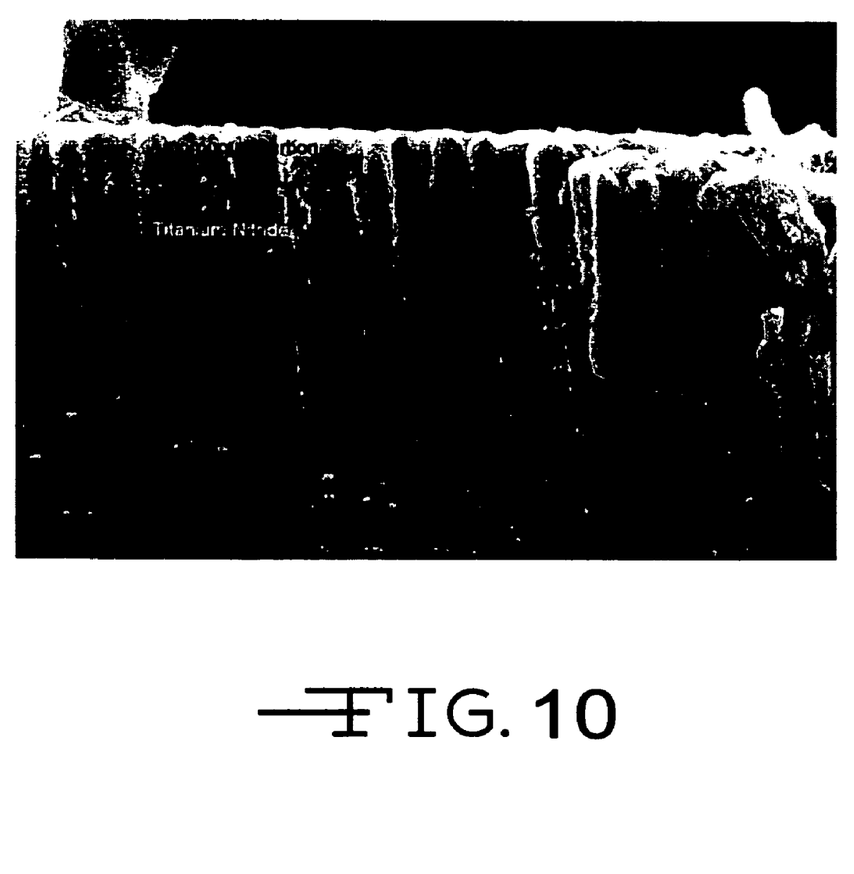
FIG. 10 is a cross-sectional photograph of the coating shown in FIG. 9. The width of field shown is 6.8 µm

The photographs in FIGS. 8 to 10 show the microstructures associated with the above polarization results. In particular, FIG. 8 shows the surface of a single particle in a sintered platinum/10% iridium electrode coating with a 200 nm thin film sputtered carbon coated directly on to the surface thereof. This electrode had a polarization of −139 mV. FIG. 9 shows the surface of a single particle in a sintered platinum/10% iridium electrode with a 200 nm thin film sputtered nitrogen-doped carbon overlayer coated onto a high specific surface area sputtered TiN intermediate layer. This electrode had a polarization of −43 mV. FIG. 10 is a cross section (fracture) of the coating shown in FIG. 9 where each TiN column is clearly tipped with nitrogen-doped amorphous carbon.

Accordingly, increasing the surface area of the sputtered carbon layer by means of an intermediate layer of high surface area columnar titanium nitride significantly reduces the polarization of an implantable electrode. Doping the amorphous carbon with nitrogen, by adding nitrogen to the sputter process gas, further reduces polarization.

EXAMPLE II

Electrode with Sintered Platinum/10% Iridium Coating Having a Sintered Diamond Intermediate Layer and a Sputtered Carbon Overlayer A porous sintered single layer of doped diamond powder having a particle size of about 3 μm was sintered to a substrate consisting of porous sintered platinum/10% iridium particles. The platinum/10% iridium particles themselves had a pore size of about 15 μm. The diamond layer was sintered by heating to a temperature of about 800° C. to about 1,100° C. at atmospheric pressure in a carbon-containing atmosphere such as a hydrocarbon partially combusted in air. Time at temperature was on the order of one minute. This conductive sintered diamond intermediate layer was then sputter coated with an outer layer of amorphous carbon, thereby improving the polarization of the resulting surface according to the present invention.

Figure 11:
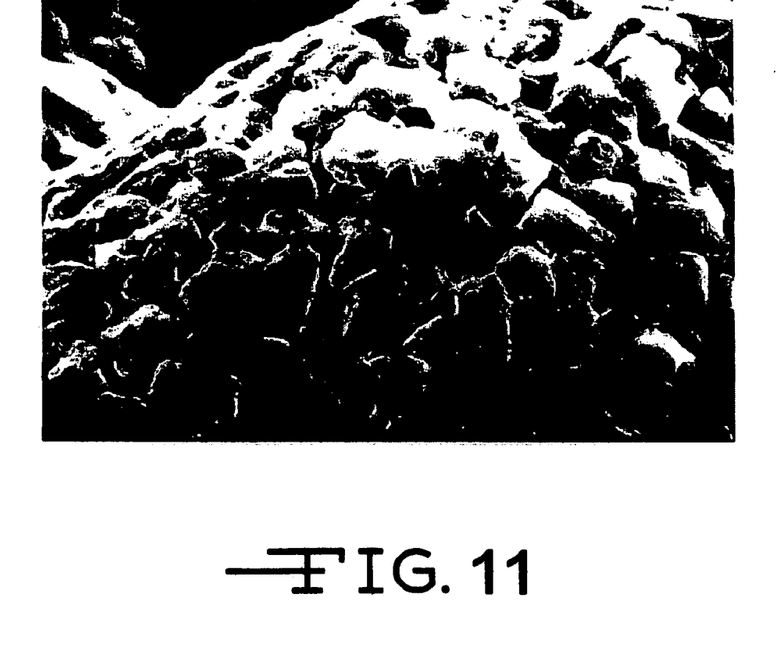
FIG. 11 is a photograph of an electrode substrate consisting of sintered particles of platinum/10% iridium coated with a fine sintered diamond powder single layer. The width of field shown is 5.5 µm.
Figure 12:
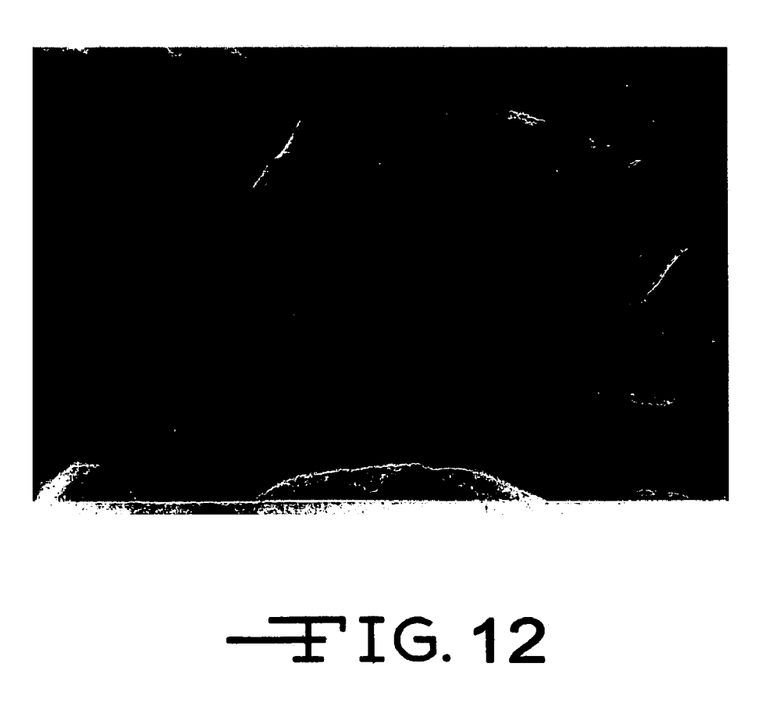
FIG. 12 is a photograph detailing the diamond powder coating on the platinum/10% iridium electrode body shown in FIG. 11. The width of field shown is 5.5 µm.

FIG. 11 is a photograph of the sintered platinum/10% iridium electrode. The sintered particles serve as a substrate for the fine sintered diamond powder intermediate layer. The enlarged photograph of FIG. 12 shows the diamond powder coating on the platinum/10% iridium electrode body. Robust necks between the diamond particles and the platinum/iridium surface indicate good adhesion of the sintered layer.

It is appreciated that various modifications to the inventive concepts described herein may be apparent to those of ordinary skill in the art without departing from the spirit and scope of the present invention as defined by the appended claims.

What is claimed is:

1. An implantable electrode, which comprises:
   a) a substrate;
   b) a biocompatible and electrically conductive intermediate coating supported on the substrate to provide the electrode with a relatively high surface area; and
   c) a carbon-containing coating comprising amorphous carbon having a random carbonaceous structure with no covalent bonding and devoid of any crystalline structure having covalent bonding in three dimensions and that conforms to the surface area of the intermediate coating.

2. The electrode of claim 1 wherein the substrate is selected from the group consisting of tantalum, titanium, zirconium, iridium, platinum, and niobium.

3. The electrode of claim 1 wherein the substrate is sintered platinum/iridium.

4. The electrode of claim 1 wherein the intermediate coating is selected from the group consisting of carbon, boron, titanium, tantalum, niobium, zirconium, titanium nitride, titanium carbide, titanium carbonitride, tantalum nitride, tantalum carbide, tantalum carbonitride, niobium carbide, niobium nitride, niobium carbonitride, zirconium oxide, zirconium nitride, zirconium carbide, titanium dioxide doped with niobium, diamond doped with boron, and mixtures thereof.

5. The electrode of claim 1 wherein the carbon-containing coating is doped with nitrogen.

6. The electrode of claim 5 wherein the nitrogen is provided in the carbon-containing coating at a concentration of about 1 ppm to about 57 atomic percent.

7. The electrode of claim 1 wherein the carbon-containing coating is characterized as having been deposited by at least one of the group consisting of sputtering, evaporation, a pyrolytic process, and chemical vapor deposition.

8. The electrode of claim 1 wherein the substrate is characterized as having its surface area increased by at least one method selected from the group consisting of sinter processing, micromachining, grit blasting, and chemical etching.

9. The electrode of claim 1 wherein the intermediate coating has a first thickness of about 0.1 μm to about 20 μm.

10. The electrode of claim 1 wherein the carbon-containing coating has a second thickness of about 10 nm to about 1.0 μm.

11. The electrode of claim 1 wherein the substrate is of platinum/10% iridium.

12. An implantable electrode, which comprises:
    a) a substrate comprising platinum and iridium;
    b) a biocompatible and electrically conductive intermediate coating comprising titanium nitride or diamond doped with boron supported on the substrate to provide the electrode with a relatively high surface area; and
    c) an amorphous carbon-containing coating having a random carbonaceous structure with no covalent bonding and devoid of any crystalline structure having covalent bonding in three dimensions and that conforms to the surface area of the intermediate coating.

13. The electrode of claim 12 wherein the carbon-containing coating is doped with nitrogen.

14. A method for providing an implantable electrode, comprising the steps of:
    a) providing a substrate comprising tantalum, titanium, zirconium, niobium, platinum, and iridium;
    b) coating an intermediate layer selected from the group consisting of carbon, boron, titanium, tantalum, niobium, zirconium, titanium nitride, titanium carbide, titanium carbonitride, tantalum nitride, tantalum carbide, tantalum carbonitride, niobium carbide, niobium nitride, niobium carbonitride, zirconium oxide, zirconium nitride, zirconium carbide, titanium dioxide doped with niobium, diamond doped with boron, and mixtures thereof on the substrate to provide the electrode with a relatively high surface area;
    c) sputtering a carbon-containing coating comprising amorphous carbon having a random carbonaceous structure with no covalent bonding that conforms to the surface area of the intermediate layer; and
    d) utilizing the coated substrate as an implantable electrode.

15. The method of claim 14 including doping the amorphous carbon with nitrogen.

16. The method of claim 14 including providing the intermediate coating having a first thickness of about 0.1 μm to about 20 μm and the carbon-containing coating having a second thickness of about 10 nm to about 1.0 μm.

17. The method of claim 14 including providing the substrate of platinum/10% iridium.

\* \* \* \* \*

UNITED STATES PATENT AND TRADEMARK OFFICE
CERTIFICATE OF CORRECTION

PATENT NO. : 7,079,903 B2
APPLICATION NO. : 10/792315
DATED : July 18, 2006
INVENTOR(S) : O'Brien It is certified that error appears in the above-identified patent and that said Letters Patent is hereby corrected as shown below:

Col. 2, line 57, delete ">-45 mV" and insert --<-45 mV--.

Signed and Sealed this

Twenty-first Day of November, 2006

JON W. DUDAS
*Director of the United States Patent and Trademark Office*